United States Patent [19]
Fisher et al.

[11] Patent Number: 5,557,263
[45] Date of Patent: Sep. 17, 1996

[54] SYSTEM FOR DETECTION OF ELECTRICALLY CONDUCTIVE FLUIDS

[75] Inventors: Larry F. Fisher, North Bend; Oscar E. Johnson, Coos Bay, both of Oreg.

[73] Assignee: Health Sense International, Inc., Coos Bay, Oreg.

[21] Appl. No.: 104,122

[22] PCT Filed: Jul. 20, 1993

[86] PCT No.: PCT/US93/07061
§ 371 Date: Jul. 20, 1993
§ 102(e) Date: Jul. 20, 1993

[87] PCT Pub. No.: WO94/02918
PCT Pub. Date: Feb. 3, 1994

Related U.S. Application Data

[63] Continuation-in-part of Ser. No. 918,273, Jul. 22, 1992, abandoned.

[51] Int. Cl.⁶ ............................................. G08B 21/00
[52] U.S. Cl. .......................... 340/605; 340/603; 340/604; 340/573; 200/61.04; 128/886; 604/361
[58] Field of Search ............................ 340/603, 604, 340/605, 573, 539; 200/61.04, 61.05; 128/886; 604/361

[56] References Cited

U.S. PATENT DOCUMENTS

| | | | |
|---|---|---|---|
| 3,460,123 | 7/1965 | Bass. | |
| 3,530,855 | 9/1970 | Balding | 128/138 |
| 3,778,570 | 12/1973 | Shuman | 200/61.05 |
| 4,106,001 | 8/1978 | Mahoney | 340/604 |
| 4,191,950 | 3/1980 | Levin et al. | 340/604 |
| 4,205,672 | 6/1980 | Dvorak | 340/604 X |
| 4,212,295 | 7/1980 | Snyder | 128/138 |
| 4,356,818 | 11/1982 | Macias et al. | 128/138 |
| 4,539,559 | 10/1985 | Kelly et al. | 340/573 |
| 4,704,108 | 11/1987 | Okada et al. | 604/361 |
| 4,738,260 | 4/1988 | Brown | 128/138 |
| 4,800,370 | 1/1989 | Vetecnik | 340/573 |
| 4,977,906 | 12/1990 | Di Scipio | 128/885 |
| 5,036,859 | 8/1991 | Brown | 128/734 |

OTHER PUBLICATIONS

Travis Industries, Coos Bay, Oregon, Wet–No–More Product Brochure, ©1987.
Sears Advertisement—Lite–Alert and Wee Alert, p. 9, prior to Jul. 1991.
Electronic Monitors, Inc., Euless, Texas, Product Advertisement "An Answer for a Too–Often Unasked Question," 5 pp., 1982.
Star Child/Labs, Aptos, CA Product Advertisement "You really can help your child *STOP* bedwetting . . . introducing SleepDry™ with Starry," 4 pp., prior to Jul. 1991.
Ideas for Living, Boulder, Colorado, Product Advertisement," Potty Pager," 3 pp.

*Primary Examiner*—John K. Peng
*Assistant Examiner*—Edward Lefkowitz
*Attorney, Agent, or Firm*—Chernoff, Vilhauer, McClung & Stenzel

[57] ABSTRACT

Apparatus for detecting the presence of electrically conductive fluids, including urine and other body fluids such as exudate from wounds, includes spaced-apart electrodes (44, 46, 96, 98) covered by absorbent material (58, 106, 108, 126, 128), together with a housing (30, 86, 154) containing a signaling device (32, 152, 172, 175) which produces a palpable vibration, a sound, a light, or a radio signal when fluid in the absorbent material provides a conductive path between the electrodes. Spring contacts (50, 138, 146) on the housing provide reliable connections with the electrodes and also serve to attach the housing of the signaling device (32) to structure (12, 78) supporting the absorbent material, and may also be used to attach the absorbent material to the housing in embodiments where the housing is otherwise supported. Encoded signals from many such sensors (160, 170) can be identifiably related to and recorded so as to be machine-retrievable together with other patient data and analyzed statistically by a computer (178, 183).

39 Claims, 11 Drawing Sheets

Fig. 21

SYSTEM FOR DETECTION OF ELECTRICALLY CONDUCTIVE FLUIDS

This application is a continuation-in-part of U.S. patent application Ser. No. 07/918,273, filed Jul. 22, 1992, now abandoned.

BACKGROUND OF THE INVENTION

The present invention relates to detection of electrically conductive fluids, and in particular to detecting and signaling the release of bodily fluids from human beings or animals.

For many years the objective of electrically detecting and indicating the presence of body fluids or other electrically conductive liquids has been pursued. Detecting such fluids often has involved using a pair of electrodes connected with a voltage source and a detector circuit intended to turn on an audible alarm when a gap between the electrodes is bridged by an electrically conductive fluid.

Devices for detecting body fluids are desired particularly for assisting in the prevention of diaper rash, for potty training of infants, and in curing enuretic youngsters, as well as for detecting the leakage of blood or other fluids after surgery and invasive diagnostic procedures. Such devices are also desired to monitor and record urinary incontinence and to facilitate better care for pressure sores in chronically bedridden persons.

Such devices could also be useful for detecting leaks in domestic hot water heaters or other liquid storage devices.

Previously available devices for use to detect human body fluids have many disadvantages. For example, some prior art devices are too bulky and uncomfortable for use in the groin area for monitoring urinary incontinence. Some prior art devices use cumbersome and unsafe long electric wires to interconnect the necessary component parts.

Other drawbacks of previously available devices include sensors which are too large or too small, are not shaped properly, or are made of materials which are not compatible with the human body or other intended environment. In particular, prior art devices have not satisfactorily provided for early detection of small amounts of body fluids. Also, many prior art devices are too expensive to manufacture economically or are impractical to use.

What is desired, then, is a system including an improved sensor and an associated alarm system for reliably and consistently detecting and signaling the presence of electrically conductive fluids under all conditions of use, without false alarms. Such a sensor should be of small size, comfortable to use, easy to maintain, clean, and prepare for reuse, self-powered, and portable. Preferably, a system incorporating such a sensor should have the ability to provide signals to remote monitors for collection and analysis of data, and should be simple to use.

The present invention provides improved apparatus and a method for its use to overcome the aforementioned shortcomings of the prior art and, in particular, provides an improved, simple, and versatile device for signaling the presence of electrically conductive fluids, such as urine, wound exudate, feces, blood, and water, and also provides a disposable absorbent pad for use in detecting such electrically conductive fluids.

An important feature of one embodiment of the present invention is the use of comfortable, soft, non-absorbent material to support an absorbent sensor and a housing for a signaling device including an electrical circuit which form parts of the device.

In one embodiment of the invention a fluid-absorbent sensing pad has two apart-spaced electrodes, included in the structure of the absorbent pad and available to be connected electrically to the signaling device.

One embodiment of the invention provides a sensing pad whose design and shape provide comfortable positioning and detection of even very small amounts of body fluids for either male or female users.

It is a feature of one embodiment of the present invention that the fluid-detecting electrode system is compatible with different signaling devices that provide vibratory, audible, visible, or wireless signals.

One embodiment of the invention provides a disposable fluid-absorbent sensor material which can be cut to a desired length from a continuous roll.

One embodiment of the invention includes a radio transmitter and an encoding device for sending a signal which is identifiably encoded for reception and interpretation by a remotely located receiver, which may be portable.

In one embodiment of the invention encoded information may include identification of the source of the encoded signal, while equipment associated with the receiver can record the received signal identification information as well as time of receiving a signal, and can then compute elapsed time since an earlier signal was received, and other information.

One embodiment of the invention includes the use of an FM radio transmitter which transmits on the commercial FM broadcast frequency band. Signals from such an FM transmitter can be received by conventional domestic radio receivers, enabling most users to have more than one remote receiver.

The foregoing and other objectives, features, and advantages of the invention will be more readily understood upon consideration of the following detailed description of the invention, taken in conjunction with the accompanying drawings.

DETAILED DESCRIPTION OF THE PREFERRED EMBODIMENTS

Referring now to the drawings which form a part of the disclosure herein, and with particular reference to FIGS. 1–6, an apparatus for detecting the presence of electrically conductive fluids, in the form of a bed wetting detector 10, includes a sensor carrier assembly 12 having a flat, generally rectangular configuration adapted to fit, for example, against the front of a wearer's night clothes as support for the detector 10. The carrier assembly 12 includes a pair of alligator clips 14, one attached at each end, as one way to attach the carrier assembly 12 to a person's clothing, such as the elastic waistband 16 of a pair of underpants, to keep it in a desired location in which a sensor portion 18 is best positioned to receive and absorb urine when the person wearing the device first begins to urinate while sleeping.

Figure 1:
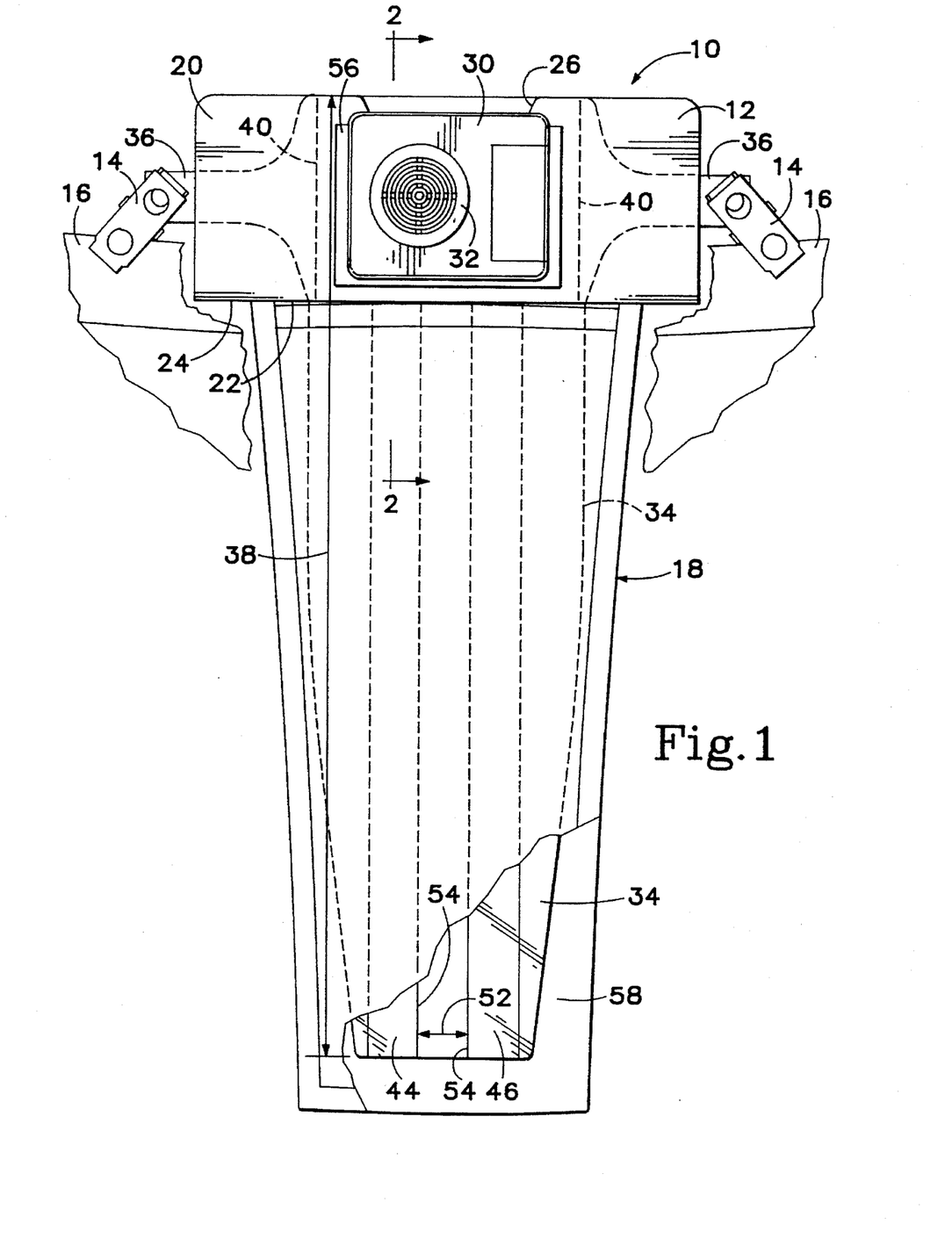
FIG. 1 is a front view of a bed-wetting detection device embodying the present invention.
Figure 2:
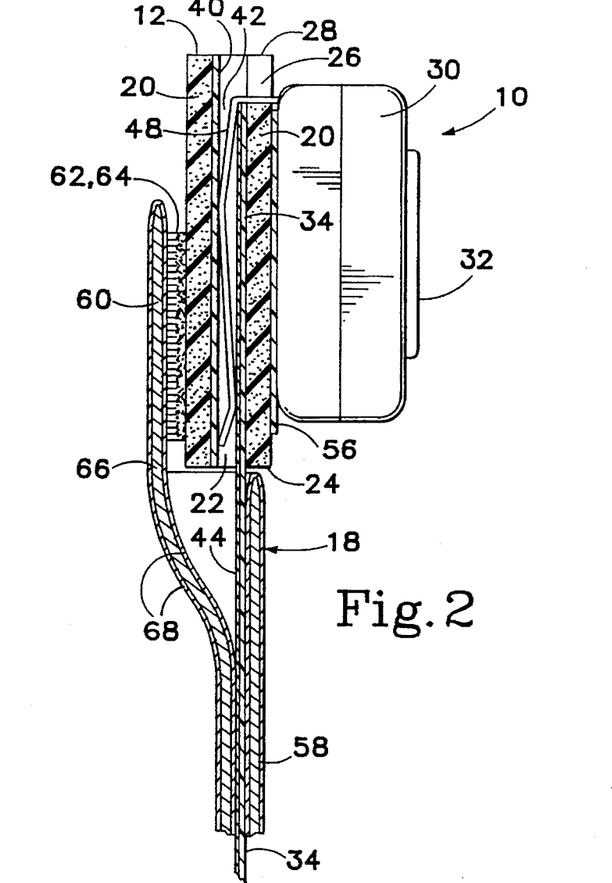
FIG. 2 is a sectional view of the device shown in FIG. 1, taken along line 2—2.
Figure 3:
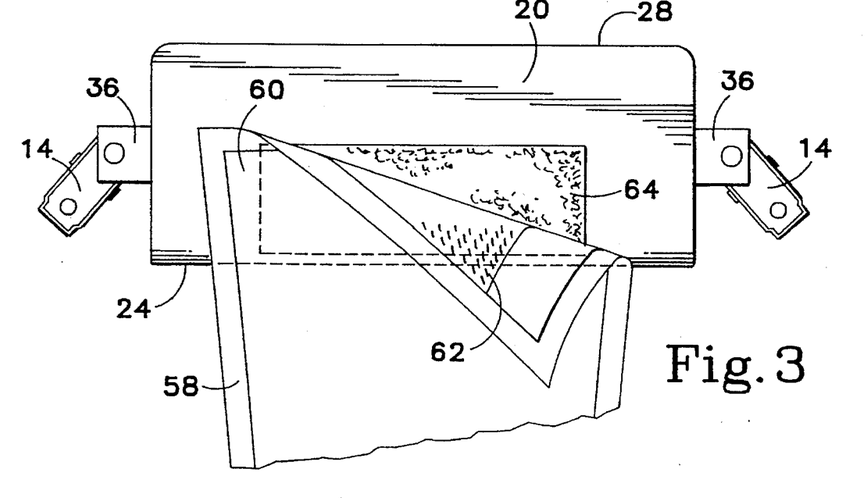
FIG. 3 is a rear view of the carrier assembly portion of the bed-wetting detection device shown in FIG. 1, together with a portion of an absorbent sensor pad and a fastener for attaching the pad to the carrier assembly.
Figure 4:
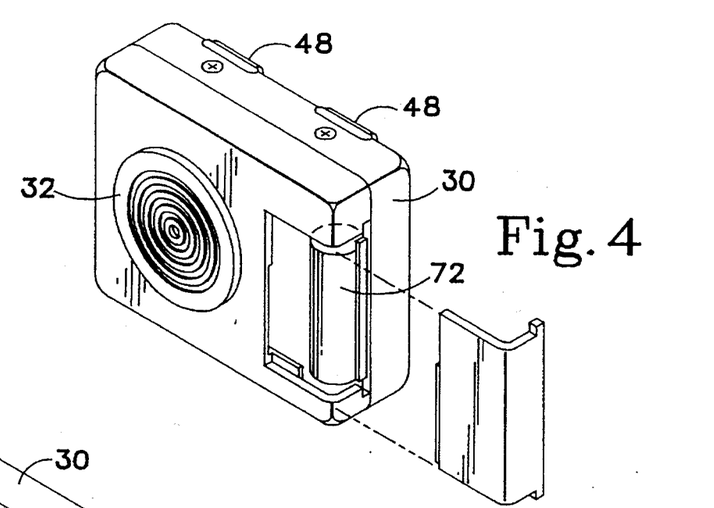
FIG. 4 is a perspective view of a housing for electronic components of a signaling device which is a part of the apparatus shown in FIG. 1.
Figure 5:
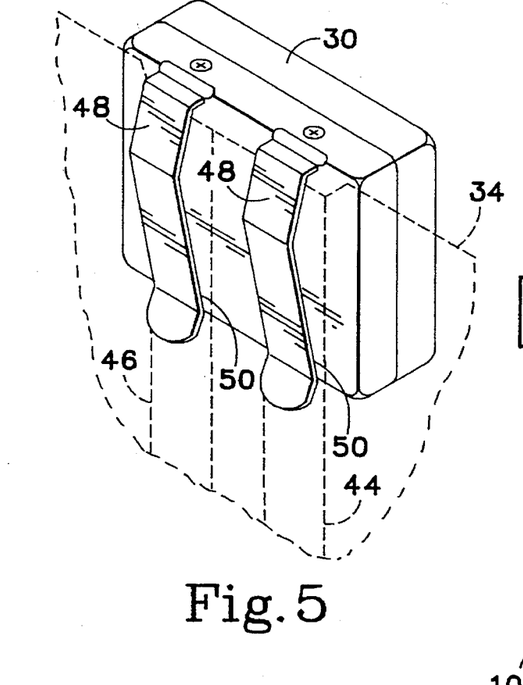
FIG. 5 is a perspective view, taken from the opposite side, of the housing for electrical components shown in FIG. 4.

The carrier assembly 12 is constructed of a sheet 20 of closed-cell polymeric foam material which may be 3 mm thick, for example, folded along a central slit 22 to define a horizontal bottom 24 of the carrier assembly. A recess 26 is defined on the front part of the carrier assembly 12 by a cutout in the top margin 28 of the folded sheet 20, providing a convenient location for attachment of a housing 30 containing electrical circuit components including a signaling device 32.

The sensor portion 18 of the device 10 is reusable and includes an electrode-carrying member 34 in the form of a backing layer of sheet plastic material such as polyvinylchloride 0.50 mm thick having a pair of opposite longitudinal margins, an upper portion of each of which extends laterally defining tabs 36 to which the alligator clips 14 are attached. The electrode-carrying member 34 may, for example, have a length 38, of about 23 cm overall, with about 18.7 cm depending downward below the central slit 22 in the closed-cell foam material of the sheet 20. The depending portion of the electrode-carrying member in a preferred embodiment of the invention is 7 cm wide over approximately its upper half, its lower half tapering to a width of approximately 4.5 cm at its lower end.

A rectangular piece 40 of flexible plastic material such as polyvinylchloride 0.25 mm thick extends lengthwise between the opposite halves of the folded sheet 20 of closed-cell foam material and is attached along its vertical ends to the rear side of the upper portion of the electrode-carrying member 34. The inner surfaces of the sheet 20 of closed-cell foam are attached to the flexible plastic material of the piece and of the electrode-carrying member by an adhesive, such as ADCHEM 5008B, available from Adchem Corporation of Westbury, N.Y. A space 42, open at its top and bottom is thus defined between the piece 40 of flexible plastic material and the upper portion of the electrode-carrying member 34.

Two parallel, flexible electrodes 44, 46 are attached to the electrode-carrying member 34 on its rear side, that is, the side facing toward the body of the user of the device. The electrodes 44, 46 are thus exposed, spaced apart from and parallel with each other, within the space 42 defined between the piece 40 of flexible plastic material and the electrode-carrying member 34.

Figure 6:
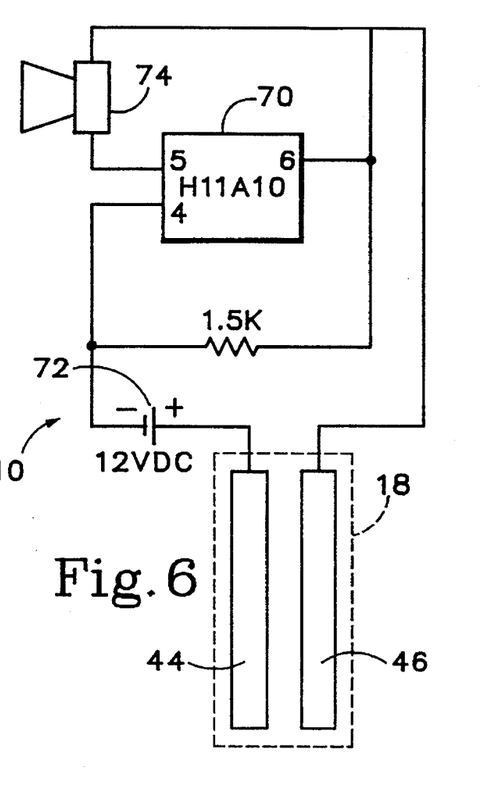
FIG. 6 is an electronic circuit diagram for an audio-output alarm which is part of a signaling device for use in the apparatus shown in FIG. 1.

The housing 30 is attached to the carrier assembly 12 by a pair of spring fingers 48 of resilient sheet metal, each of which is electrically connected appropriately to the electronic circuit components contained within the housing 30, as shown in FIG. 6, and each of which also includes a contact portion 50. The resilient spring fingers 48 attached to the housing bring each of the contact portions 50 into mechanical and electrical contact with a respective one of the electrodes 44, 46 within the space 42 defined between the flexible plastic 40 and the electrode-carrying member 34. Preferably, each of the fingers 48 has an upturned tip, to facilitate sliding the housing into position with the fingers 48 in the space 42, with each contact portion 50 contacting a respective one of the electrodes 44, 46.

Each of the electrodes 44, 46 is a strip of conductive flexible polyimide material impregnated with carbon black, such as that available from DuPont Electronics of Wilmington, Del., and known as KAPTON 400XC250, which has a suitably low resistivity of 250 ohms/sq. Each of the electrodes 44, 46 is approximately 1.3 cm wide, and a spacing 52 of approximately 1.1 cm is provided between the medial margins 54 of the two electrodes.

Preferably, an additional piece 56 of flexible plastic is attached by an adhesive to the front face of the carrier assembly to protect the closed-cell foam material of the sheet 20 from possible abrasion by the surface of the housing 30, and to facilitate removal and replacement of the housing 30 from and onto the carrier assembly 12.

An absorbent sleeve 58 fits around the electrode-carrying member 34 and the electrodes 44, 46, fitting snugly against the bottom 24 of the carrier assembly 12, adjacent the central slit 22. A flap 60 extending upward on the rear side of the sleeve 58 carries a small patch 62 of the hook-bearing material of a hook-and-loop fastener system such as that known by the trademark Velcro®, while a patch 64 of the loop-bearing material of the fastener system is attached, as by an adhesive, to the rear surface of the sheet 20 of closed-cell foam material of the carrier assembly 12, so that mating the two fastener materials 62, 64 holds the sleeve 58 appropriately in position covering the depending portions of electrode-carrying member 34 and the electrodes 44, 46.

The sleeve 58 is made of an absorbent material which is preferably washable, such as a central layer 66 of a batting of polyester fibers, covered on opposite faces by layers 68 of thin, fluid-absorbent cloth such as a cotton-polyester blend, which may be quilted, with front and rear panels of the resultant three-layer fabric being sewn together along their respective longitudinal margins and bottom margin. The entire sensor portion 18, including the sleeve 58 and the electrode-carrying member 34, is flexible but not too bulky to be worn comfortably within a user's underwear.

Referring to FIG. 6, the bedwetting detector 10 includes an audio alarm which may be contained as a signaling device 32 within the housing 30. An electronic switch 70, such as a Harris H11A10 photon-coupled current threshold switch, in which a solid-state gallium arsenide infrared-emitting diode is coupled with a silicon phototransistor in a dual in-line package, is connected to provide power from a battery 72 to an audio transducer 74 which may, for example, be a Series AI612 electronic solid-state audio indicator unit available from Projects Unlimited, Inc. of Dayton, Ohio, capable of providing 90 dba sound pressure at a frequency of about 400 Hz.

When a circuit is completed through an electrically-conductive fluid absorbed in the sleeve 58 in a location interconnecting the electrodes 44 and 46, the current through the electrically-conductive fluid is sufficient to turn on the electronic switch 70, providing a current path from the battery 72 through the audio transducer 74, so long as the battery 72 lasts and the circuit remains intact through the sensor portion 18 of the device. Thus, when moisture, such as a sufficient quantity of urine, completes the circuit the audio transducer 74 will produce enough noise to waken the person wearing the device 10, usually a small child, to enable the child to stop urinating and to learn to awaken before wetting the bed. The noise of the transducer 74 can be stopped by simply removing the spring fingers 48 of the housing 30 from contact with the electrodes 44, 46 within the carrier assembly 12.

Once the sleeve 58 has been made wet, it can be removed, permitting the carrier assembly 12, the electrode-carrying member 34, and the electrodes 44, 46 of the sensor portion 18 of the device, and the exterior of the housing 30, to be wiped dry. Thereafter, the sleeve 58 can be replaced with a dry one and the housing 30 can be replaced on the carrier assembly 12, allowing the bedwetting detector 10 to continue to monitor the wearer.

Figure 7:
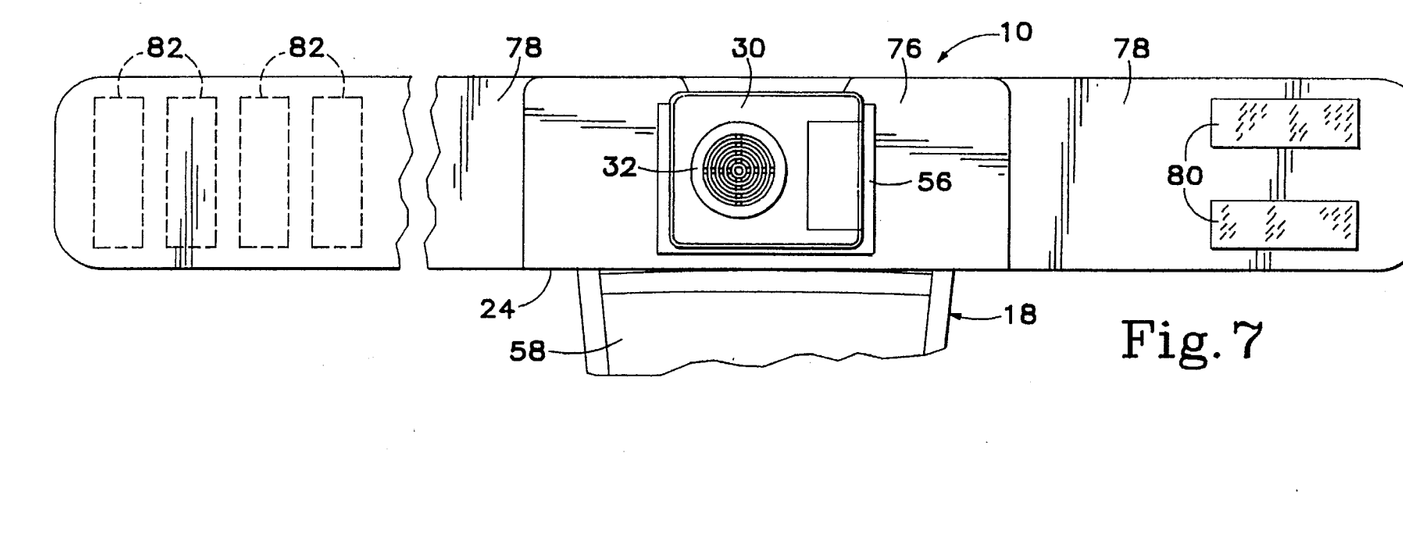
FIG. 7 is a plan view of an apparatus similar to that shown in FIG. 1 and including a belt for attachment of the device to a person.

Referring to FIG. 7, as an alternative embodiment of the apparatus shown in FIGS. 1–6, a carrier assembly 76 may include, instead of the pair of alligator clips 14 at the ends of the carrier assembly 12, a belt 78 of closed-cell foam material similar to that of the sheet 20 of the body of the carrier assembly 12. The belt 78 is equipped with mating patches 80, 82 of hook-and-loop fastener material, and excess length of the belt can be trimmed easily, so that the device can be used with people of different sizes.

Referring next to FIGS. 8–12, a body fluid detecting device 84 which is another embodiment of the invention includes a housing 86 for electronic circuitry similar to the housing 30 previously described. It includes an alligator clip 88 attached to the housing, as by a looped strip 90 of flexible plastic material engaged movably through an opening defined by a small strip 92 of plastic material fastened to the housing.

Figure 8:
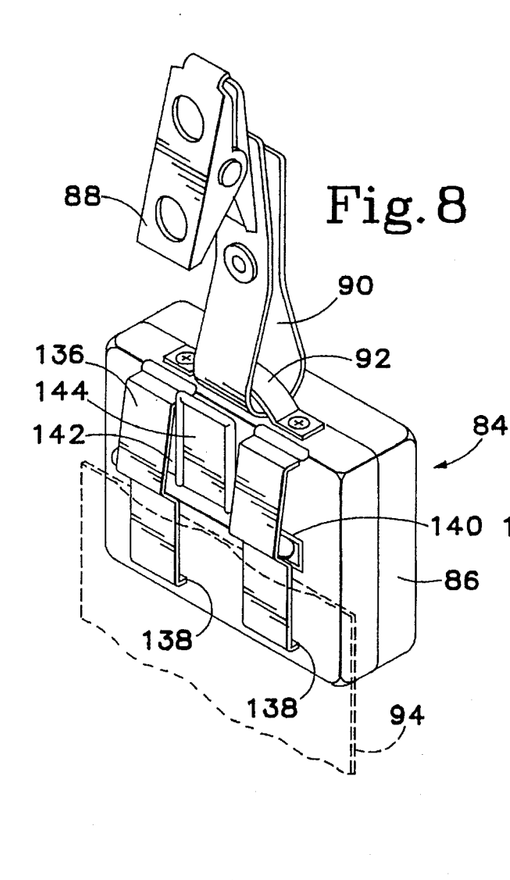
FIG. 8 is a perspective view of a device for detecting conductive fluid such as body fluids which is an alternative embodiment of the invention.
Figure 9:
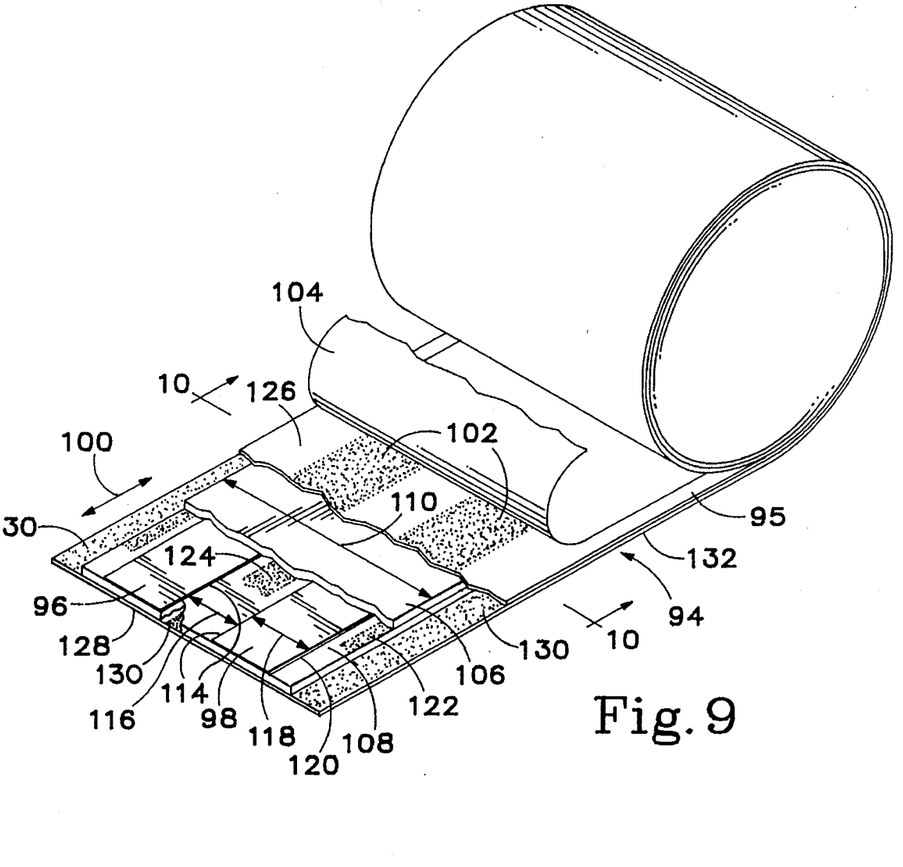
FIG. 9 is a perspective view of a roll of absorbent sensor material including absorbent layers and electrodes, according to the invention, useful as a disposable sensing pad material in detecting electrically conductive fluids in accordance with the present invention.
Figure 10:
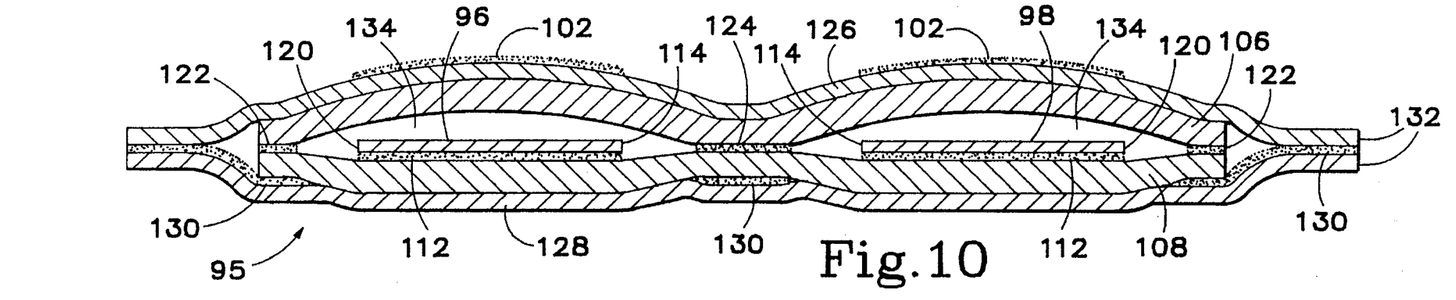
FIG. 10 is a sectional view, taken along line 10—10, showing the structure of the material shown in FIG. 9.

Instead of the carrier assembly 12 and the associated reusable sensor portion 18, however, the body fluid sensing device 84 shown in FIGS. 8–12 utilizes a disposable sensing pad 94 of absorbent sensor material 95 which includes a pair of electrodes 96, 98. The absorbent sensor material of the disposable sensing pad 94, as shown in FIGS. 9 and 10, has the form of an elongate strip and may be provided in the form of a roll of such material 95 which can be cut to a desired or required length. For example, for use to detect urinary incontinence, a strip of the absorbent sensor material 95 may be cut approximately the same length, in the direction indicated by the arrow 100, as the length of the electrode-carrying member 34 of the reusable sensor 18 described previously, or to a shorter or longer length, depending upon the size of the person using the device.

Two strips 102 of an adhesive material, normally covered by an easily removable protective paper tape 104, are available on one face of the disposable sensing pad 94, to be used to attach the disposable sensing pad 94 to a person's clothing. Where the device is used to detect seepage from a wound, the adhesive material may be used to attach the absorbent sensor material 95 to person's skin, instead, or to a portion of a bandage, as appropriate. An adhesive material such as that available in the form of a spirally rolled strip of adhesive and a protective paper layer from the Minnesota Mining and Manufacturing Company of Minneapolis, Minn., as its No. 924 adhesive is suitable, although an adhesive applied in fluid form and then covered with the protective paper tape 104 during the process of manufacture of the absorbent sensor material 95 would also be suitable.

The absorbent sensor material 95 of the disposable sensing pad 94 is of multi-layered construction, including a pair of inner layers 106, 108 of a continuous, absorbent soft paper or similar material having a width 110 of about 4.5 cm. The pair of flexible electrodes 96, 98 may be ribbon-like strips of polyester plastic provided with a conductive metallic coating, such as aluminum, on each face, and are attached by layers 112 of an adhesive to the sheet 108 of paper, with one metallized face of each electrode facing away from the sheet 108. The closer, or medial, longitudinal margins 114 of the electrodes are spaced apart from one another by, a distance 116 of, for example, 1.2 cm, and each electrode has a width 118 of 1.2 cm, leaving three to four tenths of a centimeter of the width 110 of the paper clear alongside the outer or lateral longitudinal margin 120 of each electrode.

The other sheet 106 of the absorbent soft paper overlies the sheet 108 to which the electrodes 96, 98 are adhesively attached, and the two sheets 106, 108 of absorbent paper are attached to each other by strips 122 of adhesive material along their longitudinal margins, and by adhesive material, preferably in the form of a continuous strip 124, located between the two electrodes 96, 98 to prevent them from being pushed into contact with each other as a result of the disposable sensing pad 94 bending to conform to a person's body or clothing during use of the device.

On each side of the disposable sensing pad 94 an outer layer 126 or 128 of flexible fluid-conducting absorbent material overlies the inner layers 106, 108. The outer layers 126, 128 are attached to each other and to the margins of the inner layer of material, as by adhesive material 130 interconnecting the longitudinally-extending lateral margins 132 of the outer layers with each other and also attaching the outer layer 128 to the inner layer 108, to which the electrodes 96, 98 are adhesively attached. Instead of the adhesive materials 112, 122, 124 and 130, ultrasonic welding may be used to bond together the inner and outer layers 106, 108, 126 and 128 if a weldable bonding agent, such as latex, is included in the materials of the inner or outer layers.

Figure 11:
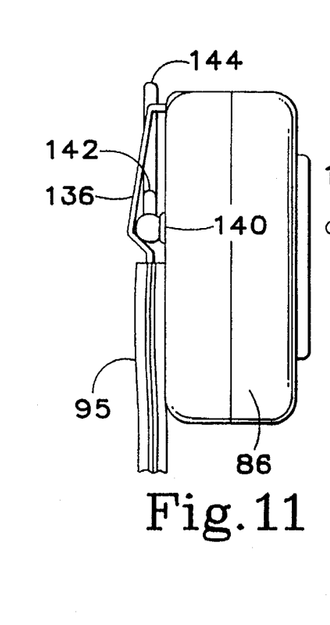
FIG. 11 is a side elevational view of the housing shown in FIG. 8, together with a disposable sensing pad.

Each electrode 96, 98 is exposed within a respective tube 134 formed by the opposing surfaces of the inner layers 106, 108 of absorbent soft material. The spring fingers 136 on the outside of the housing 86, each electrically connected appropriately with the electrical components contained within the housing, fit within the tubes 134. The contacts 138 located on the spring fingers 136 thus make electrical contact with the electrodes 96, 98, while the electrodes 96, 98 are kept separate from each other by the bonded-together portions of the inner layers 106, 108.

The inner layers 106, 108 may, for example, be of a paper product available from Fort Howard Paper Company of Green Bay, Wis. as its grade 835 dry form 8-ply lightweight fabric made of bleached pulp. The outer layers 126, 128 may be of a rayon apertured fabric, print bonded with a rope pattern, and available from Fort Howard Paper Company of Green Bay, Wis., as its grade 920 Carded™ material. The material of the outer layers 126, 128 has a lower absorbent capacity but a higher wet tensile strength than the material of the inner layers 106, 108, so that the outer layers provide strength to the disposable sensing pad 94 and allow moisture to pass quickly to the inner layers 106, 108 to be absorbed and brought into contact with the electrodes 96, 98 to complete an electrical path between the electrodes.

Figure 12:
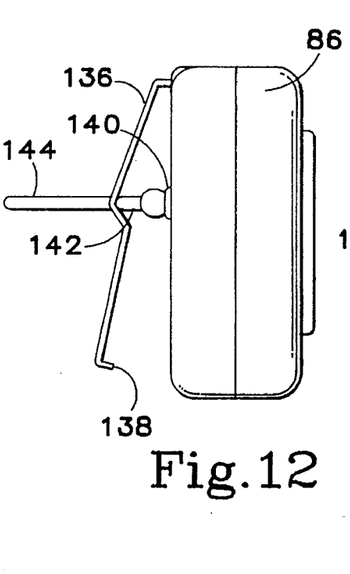
FIG. 12 is a view similar to FIG. 11, showing the spring fingers held in a contact-releasing position by a cam.

As shown in FIGS. 8, 11 and 12, the spring fingers 136 include down-turned tips as the contacts 138, to provide electrical contact with the electrodes of the absorbent sensor material 95 of the disposable sensing pad 94. The spring fingers each include a zigzag bend, and the housing 86 includes a raised ridge 140 defining a support for a cam 142 which can be rotated toward the zigzag bend by a lever 144 to raise the contacts 138 away from the housing 86 to permit the ends of the spring fingers 136 to be inserted into the tubes 134 of the disposable sensing pad 94. When the lever 144 is returned to a position parallel with the outer surface of the housing 86 the contacts are urged against and into electrical contact with the electrodes 96, 98 by elastic spring tension in the spring fingers 136.

Figure 13:
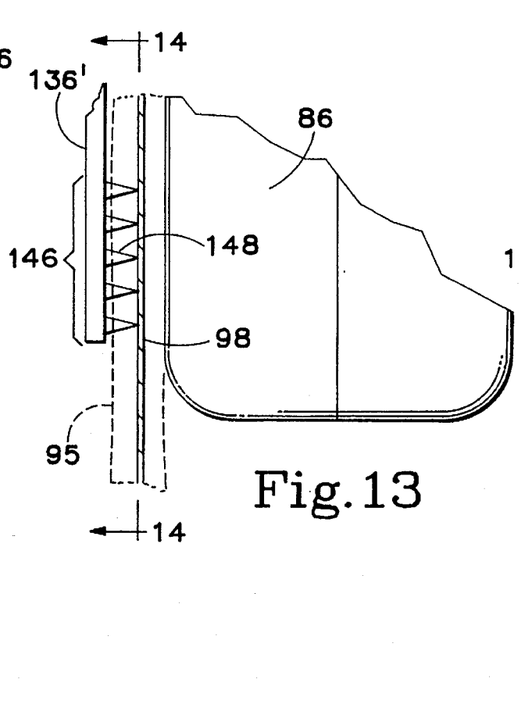
FIG. 13 is a side elevational view of a detail of a housing similar to that shown in FIGS. 8, 11 and 12, and equipped with spring fingers which include somewhat different electrical contacts.
Figure 14:
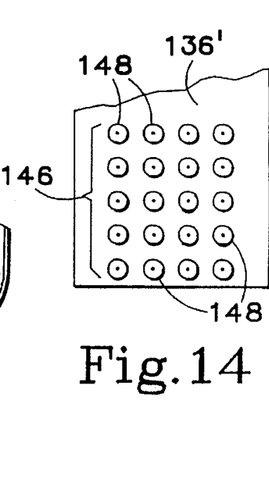
FIG. 14 is a view of a contact shown in FIG. 13, taken in the direction indicated by line 14—14.

As shown in FIGS. 13 and 14, a spring finger 136' includes a multi-tined contact 146 in place of the down-turned contacts 138 of the spring fingers 136 just previously described. Each tine 148 has a length of, for example, about 0.06 cm, long enough to extend through the outer layer 126 and inner layer 106 of the disposable absorbent sensor material 95 to make electrical contact with the electrodes without having to be inserted within the tubes. This construction permits the absorbent sensor material of the disposable sensing pad to be used to present the adhesive 102 facing in a desired direction with respect to the housing 86, to attach the sensing pad 94 either to a patient's undergarment or to a patient's skin, depending upon the application for which the body fluid detecting device 80 is being used. Alternatively, the tines, electrically connected, could be provided on the housing 86 with the spring fingers 136 pressing the electrodes into contact with the tines.

Figures 15, 18:
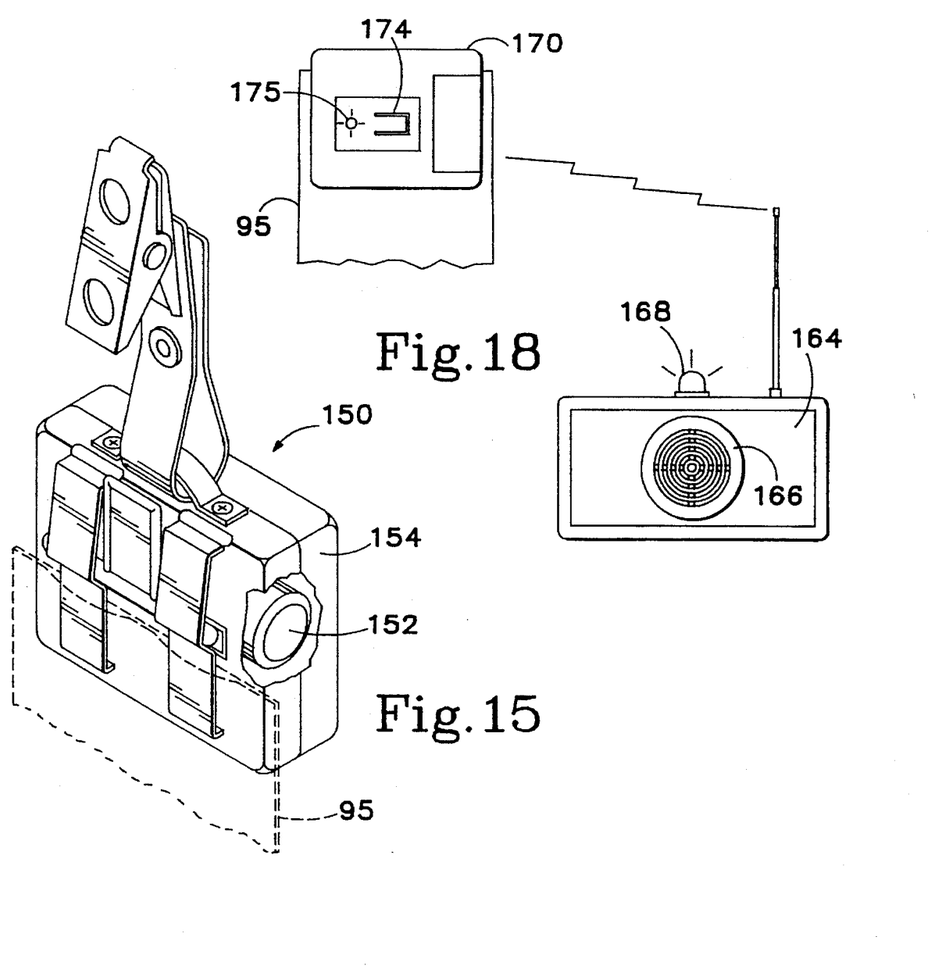
FIG. 15 is a partially cut-away view of a housing for electronic circuitry for providing a quiet signal which can be felt by the wearer of a device according to the present invention, including a clip for attachment of the housing to a person's clothing.
FIG. 18 is a view similar to FIG. 17, showing the use of a receiver in accordance with the present invention to provide a visible indication of a signal from a sensing device.
Figure 16:
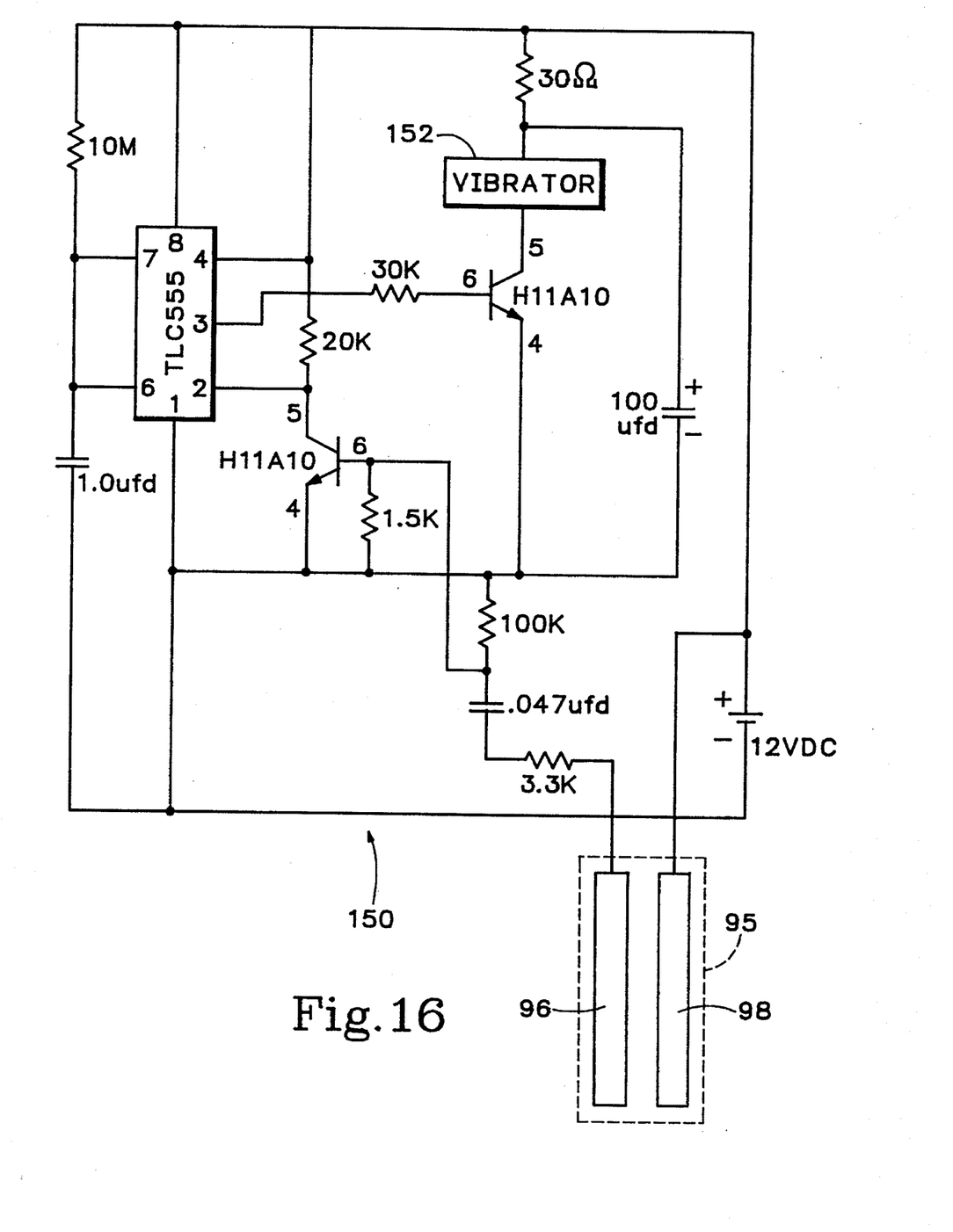
FIG. 16 is an electronic circuit diagram illustrating a circuit for use in connection with the vibrator signaling device shown in FIG. 15.

Certain people, because of medical conditions, are unable to detect normally and reliably when uncontrollable urination is about to begin. In some of such people, however, a small amount of urine, great enough to be detected by a sensing device according to the invention, leaks from the person early enough for the person, if aware of such leakage, to proceed to a toilet to complete voiding the bladder. Such persons can utilize a body fluid sensing device 150 including a vibrator 152 as its signaling device as shown in FIGS. 15 and 16. The vibrator 152 is contained within a housing 154 similar to the housing 86, and can be felt by the wearer, allowing the person wearing the device to proceed to a restroom soon enough to avoid embarrassment by wet clothing. The device 150 itself does not cause embarrassment, however, because its signal is inaudible to nearby people. This permits the person with such a medical problem to live in a substantially normal way, without having to be catheterized or to wear diapers. A suitable vibrator circuit, shown in FIG. 16, includes a TLC 555 integrated circuit available from Tandy Corporation, of Dallas, Tex., which, when connected as shown, latches in a mode providing power to the vibrator 152 once conductivity is established, even briefly, between the spring fingers 136, as by urine providing a conductive path between electrodes 96, 98 of a disposable sensing pad 94 connected to the contacts 138 of the spring fingers 136 of the housing 154. A suitable vibrator 152 is a vibration pager Model 7CE-1701 WL-00, available from Namiki Precision Jewel Co., Ltd., of Rochelle Park, N.J., which includes a small coreless DC motor and an eccentrically weighted shaft.

A reusable sensor 18 or a disposable sensor 94 according to the present invention may be used in a system containing one or more of the sensing devices, each equipped with a small, low-powered radio transmitter and one or more receivers and display devices, to monitor, for example, infants, invalids, or nursing home or hospital patients suffering from, among other things, urinary incontinence, pressure sores, surgical wounds, and other problems.

Figure 17:
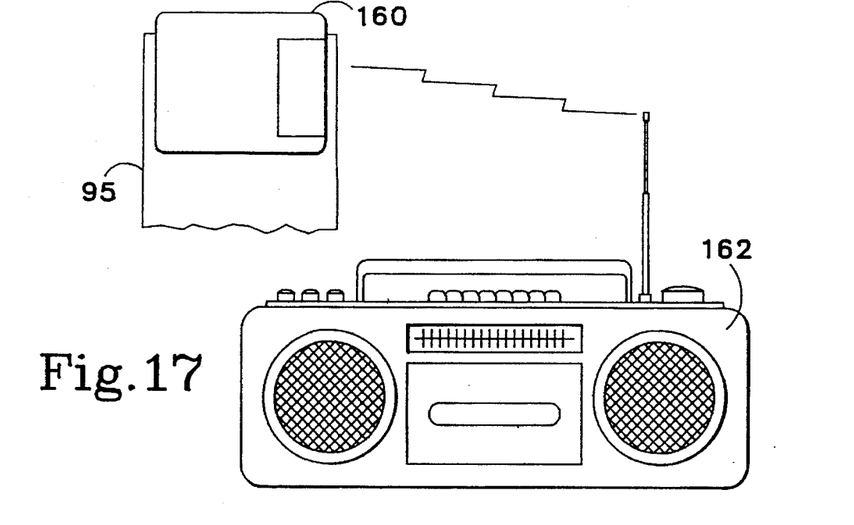
FIG. 17 is a simplified view of a system including a radio transmitter and receiver in combination with a sensor according to the present invention for detecting the presence of electrically conductive fluids.

For example, as shown in FIG. 17, in one basic form of such a system, a transmitter included in body fluid detecting device 160 connected with a sensing pad 94 (or with a reusable sensor 18) transmits at very low power on a frequency within the commercially used FM broadcast band. When an electrically conductive fluid completes the electrical path between electrodes of the sensing pad 94 the transmitter begins to transmit, continuing to transmit a signal until an FM receiver in the close vicinity, as within the same house, for example, alerts a person who can disconnect the device from the electrodes of the sensing pad 94, or until the battery powering the transmitter is exhausted. Preferably, the transmitting frequency is variable to avoid local commercial broadcast frequencies. A timing circuit could be connected to the transmitter (as in the circuit shown in FIG. 19) to limit battery drain.

A receiving device for use with such a transmitter for a single patient situation may simply be an ordinary household FM receiver 162, so that a caregiver could keep several receivers tuned, in different locations in the house, to receive a signal indicating that attention to the patient is required, or may carry a small portable FM receiver tuned to provide the signal no matter where the responsible person moves within the transmitting range of the device.

Another receiver device, as shown in FIG. 18, may be a special-purpose receiver 164 including an audible signaling device 166 or visible signaling device 168. A latch circuit is included to turn on the signaling device and keep it activated until turned off or reset by the responsible person.

Figure 19:
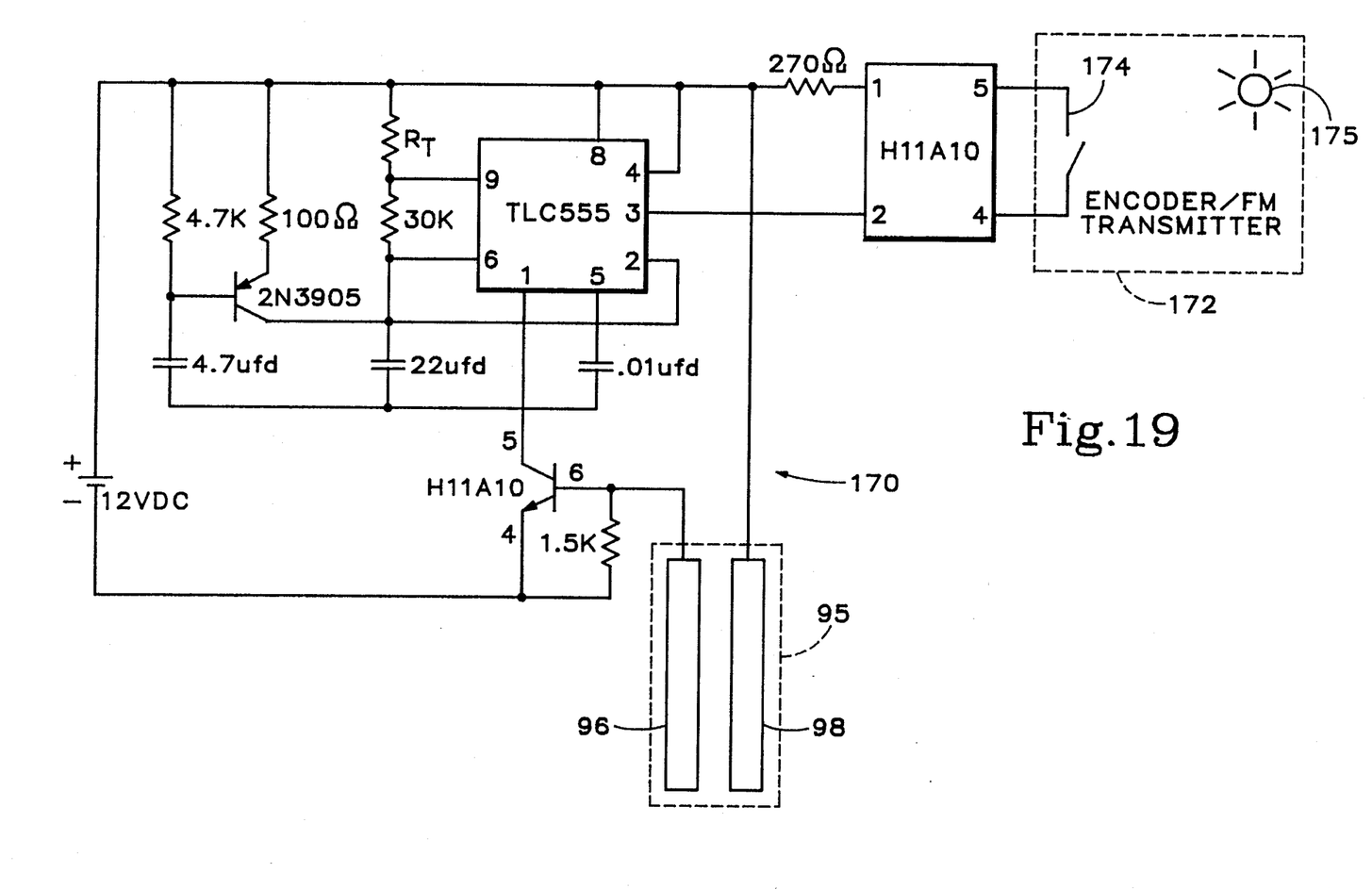
FIG. 19 is an electronic circuit diagram for a portion of a signaling device for use in accordance with the present invention, including a signal repeat timer.
Figure 20:
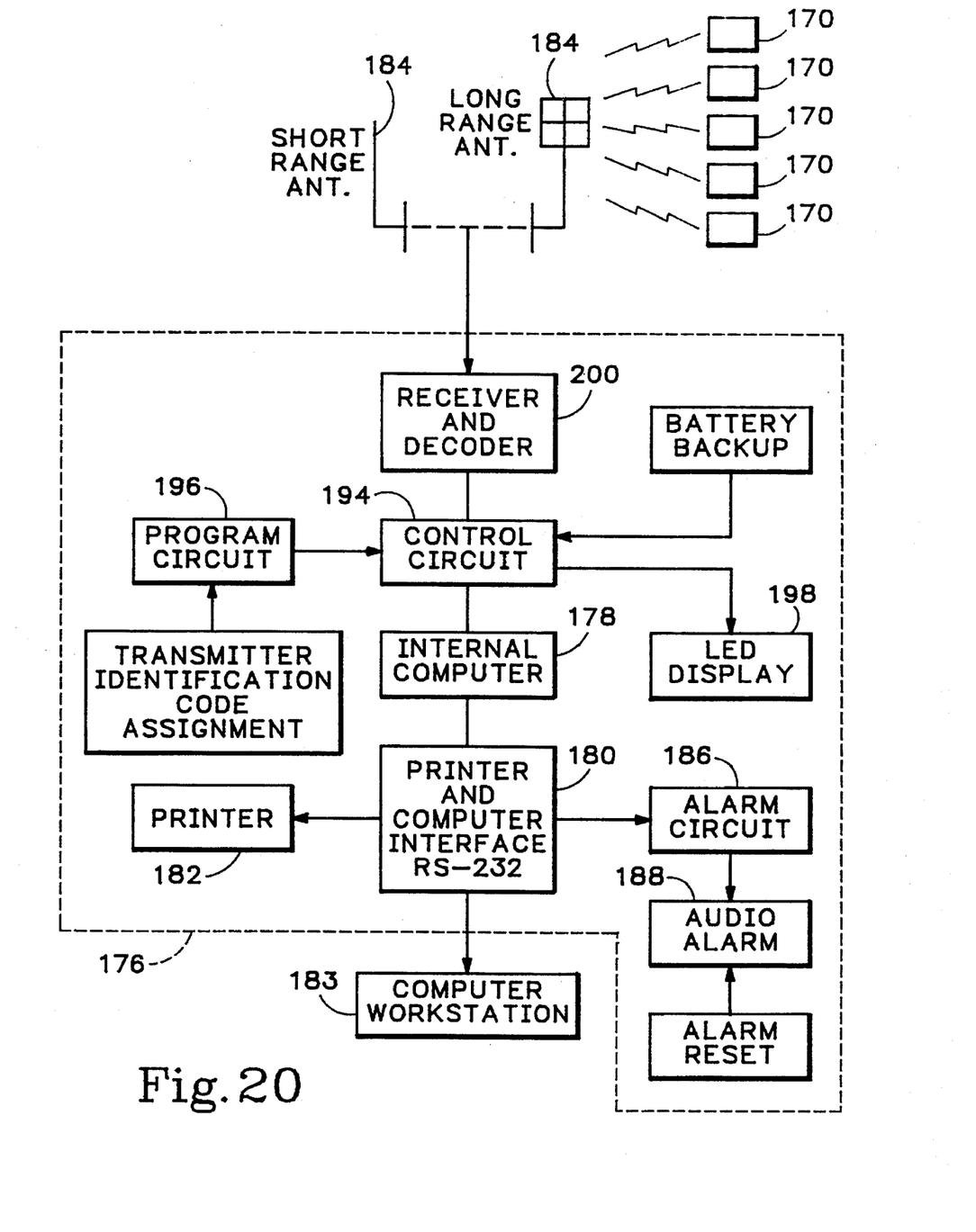
FIG. 20 is a block diagram of a system according to the present invention including several body fluid detection devices each including a wireless signaling device.
Figure 21:
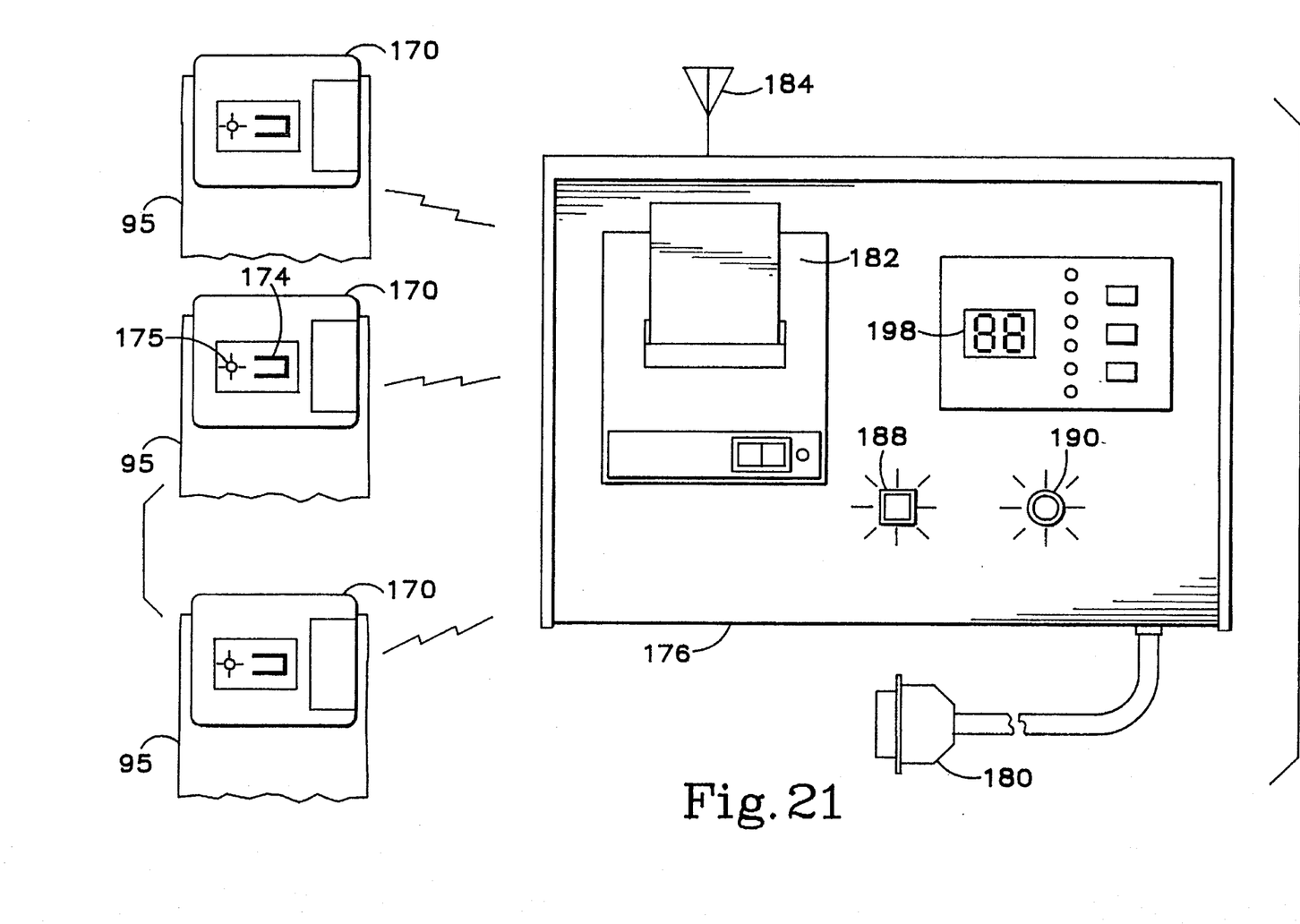
FIG. 21 is a view of a system monitoring unit and several sensing devices of a system according to the present invention.

A body fluid detecting device 170 which is another embodiment of the invention incorporates a circuit as shown in FIG. 19, and controls a transmitter 172 to provide an FM radio signal which is transmitted for only a limited time, for example one second. The transmitter 172 is reactivated periodically to send another such transmission, with a delay between transmissions which is established by the value of the resistor $R_T$. For example, when $R_T$ is 10 megohms, the delay is two minutes, and when $R_T$ is 20 megohms the delay is four minutes. (If a first encoded signal transmission is not received by the receiver 164, the next or a subsequent transmission is received by the special purpose receiver 164 and the signaling device 166 is activated and latched "on.") The included transmitter 172 is accompanied by a digital encoding device which uniquely identifies the transmitter of the device 170. A transmitter test switch 174 and an indicator lamp 175 which are also provided.

Where there are multiple patients to be monitored, as in a hospital or nursing home, a central receiving device may be used with several sensing devices 170. Referring now to FIGS. 20 and 21, the nurses' station 176 includes an internal computer 178 and an RS-232 interface 180 through which inputs and outputs to and from an external computer 183 may be directed. The station 176 includes a printer 182 on which the identity of each transmitter 172 of a sensing device 170 and the time of transmission of an incident message signal (indicating a circuit completed through sensor electrodes) or a reset message (indicating use of the transmitter test switch 174) initiates a transmission which is received by the antenna 184. The antenna 184 may be more or less efficient, depending on the needs imposed by the size of the building in which the system is used. An alarm circuit 186 responsive to signals from the computer 178 provides an audio alarm signal 188 and illuminates an indicator lamp 190 to show that a signal has been received. Control circuits 194 connected to the printer-computer interface allow a programming circuit 196 to assign identification of patients to transmitters, each of which has its own unique encoded identification signal which is transmitted as a part of the transmitter protocol each time the transmitter of a body fluid sensing device such as the device 170 is activated. A visual numerical display 198 provides an identifying display of the origin of the latest received transmission.

A receiver-decoder 200 receives each transmission and passes on the significant portion of the encoded identification signal to be processed through the control circuit 194 into the internal computer 178. These elements are included in a work station receiver available from Linear Corporation of Carlsbad, Calif. as its Linear Model AC-680 receiver, which operates in conjunction with and in response to Linear Model ACT-1/318 transmitters, each enclosed in an individual housing connected to a respective sensor such as an appropriate length of the disposable absorbent sensor material 95, or an appropriately-shaped electrode-carrying member 34 provided with a pair of electrodes 44, 46 and a corresponding sleeve 58 such as those included in the bed-wetting detection device 10 described previously, or modified in size and shape to be appropriate for sensing body fluids exuded from surgical wounds and the like or body discharges from animals, where the device is used in a veterinary application.

Data accumulated in the internal computer 178 may be transmitted through the RS-232 interface 180 to the external computer 183 for assembly and calculation of statistical data, filing and retrieval, and correlation with other data concerning individual patients or groups of patients. In particular, computer-recorded photographs and medical histories of patients may be stored in a database for retrieval to evaluate patient progress and efficiency of patient care and caretaker response to body fluid loss as shown by time of receipt of incident messages and reset messages.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A sensing pad for use in detecting the presence of electrically conductive fluids, the sensing pad comprising:

(a) a first layer of a flexible fluid-absorbent sheet material;

(b) a pair of elongate flexible electrodes extending generally parallel with and spaced apart from each other and adhesively attached to said first layer, each of said electrodes having a medial longitudinal margin and a lateral longitudinal margin; and (c) a second layer of flexible fluid-absorbent sheet material overlying said electrodes and adhered to said first layer along a continuous central strip extending parallel with said electrodes and located between said electrodes, and also adhered to said first layer along a respective strip extending parallel with said electrodes and located alongside said lateral longitudinal margin of each of said electrodes, said first and second layers thereby being interconnected in the form of a pair of separately defined parallel tubes each including one of said electrodes, each of said electrodes having a respective electrically conductive surface exposed within the respective one of said tubes and each said electrode being prevented by said separate parallel tubes from touching said electrically conductive surface of the other flexible electrode of said pair.

2. The sensing pad of claim 1, each of said first and second layers having a pair of opposite longitudinally-extending lateral margins, and said sensing pad including a third layer of flexible, fluid-conducting material, said third layer overlying and adhering to one of said first and second layers along said lateral margins thereof.

3. The pad of claim 2, further including a fourth layer of flexible, fluid-conducting material, said fourth layer overlying the other one of said first and second layers and adhering to said third layer along said opposite longitudinally-extending lateral margins thereof.

4. The sensing pad of claim 1 including an outer face and adhesive means located on said outer face for selectively fastening said pad in a desired position to absorb body fluid originating from a person.

5. Apparatus for detecting the presence of electrically conductive fluid, comprising:

(a) a first layer of a flexible fluid-absorbent sheet material;

(b) at least a pair of elongate flexible electrodes extending along said first layer generally parallel with and spaced apart from each other, each of said electrodes of said pair being adhesively attached to said first layer and having a medial longitudinal margin and a lateral longitudinal margin;

(c) a second layer of flexible fluid-absorbent material overlying said electrodes and adhered to said first layer along a continuous central strip extending parallel with said electrodes and located between said electrodes, and also adhered to said first layer along a respective strip extending parallel with said electrodes and located alongside said lateral longitudinal margin of each of said electrodes, said first and second layers thereby being interconnected in the form of a pair of separately defined parallel tubes each including one of said electrodes, and each of said electrodes having a respective electrically conductive surface exposed within the respective one of said tubes and each said electrode being prevented by said separate parallel tubes from touching said electrically conductive surface of the other flexible electrode of said pair; and (d) signaling means connected electrically to said electrodes, for producing a signal in response to electrical resistance between said electrodes being below a predetermined value.

6. The apparatus of claim 5 wherein said signaling means includes a vibrator for producing said signal inaudibly.

7. The apparatus of claim 5 wherein said signaling means includes means for providing said signal visibly.

8. The apparatus of claim 5 wherein said signaling means includes means for providing said signal in an audible form.

9. The apparatus of claim 5 wherein said signaling means includes a wireless transmitter.

10. The apparatus of claim 9 wherein said wireless transmitter transmits said signal on a frequency within a commercial FM broadcast frequency band.

11. The apparatus of claim 9, further including a receiver including means for providing a humanly perceptible alarm indication in response to receiving a signal from said wireless transmitter.

12. The apparatus of claim 9 wherein said signaling means includes means for producing and transmitting a machine-intelligible message.

13. The apparatus of claim 5, including a housing containing said signaling means, and further including a spring finger mounted on said housing, said spring finger including a contact located thereon, said contact pressing against one of said electrodes, said spring finger clamping said one of said electrodes between said spring finger and said housing and said contact thereby connecting said one of said electrodes electrically with said signaling means.

14. Apparatus for detecting the presence of electrically conductive fluid, comprising:

(a) a first layer of a flexible fluid-absorbent material;

(b) at least a pair of elongate flexible electrodes extending generally parallel with and spaced apart from each other and along said first layer, each of said electrodes of said pair having a medial longitudinal margin and a lateral longitudinal margin;

(c) a second layer of flexible fluid-absorbent material overlying said electrodes and adhered to said first layer at locations between said electrodes and alongside said lateral longitudinal margin of each of said electrodes, said first and second layers thereby defining a pair of parallel tubes each including one of said electrodes, and each of said electrodes having an electrically conductive surface exposed within the respective one of said tubes;

(d) signaling means connected electrically to said electrodes, for producing a signal in response to electrical resistance between said electrodes being below a predetermined value;

(e) a housing containing said signaling means;

(f) a spring finger mounted on said housing;

(g) a contact located on said spring finger, said contact pressing against one of said electrodes and thereby connecting said one of said electrodes electrically with said signaling means; and (h) a lever-operated release cam associated with said spring finger.

15. The apparatus of claim 13, including a tine for piercing a layer of said fluid-absorbent material and electrically contacting said electrode.

16. The apparatus of claim 13 wherein said signaling means includes means for providing said signal in audible form.

17. The apparatus of claim 13 wherein said signaling means includes a wireless transmitter.

18. The apparatus of claim 17 wherein said signaling means includes means for producing and transmitting a machine-intelligible message.

19. The apparatus of claim 5 wherein said signaling means includes timing means for limiting the duration of said signal to a predetermined time.

20. Apparatus for detecting the presence of an electrically conductive fluid, comprising:

(a) a protective housing for electrical components;

(b) a signaling device contained within said protective housing;

(c) a sensor including a backing layer and at least a pair of apart-spaced electrodes of flexible electrically-conductive material adhesively mounted on said backing layer and absorbent member means associated therewith for receiving a quantity of an electrically conductive fluid and conducting said fluid into contact with said electrodes to create an electrically conductive path between said electrodes;

(d) a sensor carrier to which said sensor is attached, said sensor carrier including releasable fasteners for attaching said sensor carrier to a person's clothing in a desired location and a padding member of resilient non-absorbent sheet material defining a slit and having an upper margin extending parallel with said slit, said backing layer including an upper portion adhered to said padding member adjacent said upper margin, and a lower portion of said backing layer extending downward through said slit and below said sensor carrier, said upper portion having respective portions of said electrodes located thereon;

(e) a pair of resilient fingers mounted on said housing and resiliently gripping a portion of said padding member adjacent said upper margin and thereby attaching said housing removably to said sensor carrier; and (f) a respective contact mounted on each of said resilient fingers, said contact being pressed by said resilient finger against a portion of one of said electrodes of said sensor located on said upper portion of said backing member and thereby effecting an electrical connection between said one of said electrodes and said signaling device while attaching said housing to said sensor carrier.

21. The apparatus of claim 20 wherein said backing layer is of flexible thin sheet plastic material, a portion thereof being attached to said sensor carrier, and said absorbent member means including a sleeve enclosing respective portions of said backing layer and said electrodes.

22. The apparatus of claim 20, said absorbent member means including a tab connected with said sleeve and overlying a portion of said sensor carrier and releasably attached thereto by hook-and-loop fasteners.

23. The apparatus of claim 20 wherein said signaling means includes timing means for limiting the duration of said signal to a predetermined time.

24. The apparatus of claim 20 wherein said signaling means includes a vibrator for producing said signal inaudibly.

25. The apparatus of claim 20 wherein said signaling means includes means for providing said signal visibly.

26. The apparatus of claim 20 wherein said signaling means includes means for providing said signal in an audible form.

27. The apparatus of claim 20 wherein said signaling means includes a wireless transmitter.

28. The apparatus of claim 27 wherein said wireless transmitter transmits said signal on a frequency within a commercial FM broadcast frequency band.

29. The apparatus of claim 27, further including a receiver including means for providing a humanly perceptible alarm indication in response to receiving a signal from said wireless transmitter.

30. The apparatus of claim 20 wherein said signaling means includes means for producing and transmitting a machine-intelligible message.

31. A method for obtaining and arranging patient data, comprising:
   (a) placing an absorbent pad in position to receive and absorb a quantity of electrically conductive fluid from a patient;
   (b) placing electrodes connected to a signaling device adjacent said absorbent pad in position to be interconnected electrically by a quantity of electrically conductive fluid absorbed by said absorbent pad;
   (c) applying an electrical potential between said electrodes and detecting electrical current conducted between said electrodes by said electrically conductive fluid absorbed in said absorbent pad;
   (d) in response to detecting said electrical current between said electrodes, transmitting an encoded incident message;
   (e) receiving said encoded incident message at a location remote from said absorbent pad and recording the time of receipt of said incident message;
   (f) thereafter removing said absorbent pad and replacing it with one that is free from electrically conductive fluid absorbed therein, placing said absorbent pad in position to receive and absorb a further quantity of electrically conductive fluid from said patient, and contemporaneously transmitting an encoded reset message; and
   (g) calculating the amount of time between each incident message and the next succeeding reset message.

32. The method of claim 31, including the further step of repeating steps (b), (c), (d), (e), and (f) of claim 31 throughout an extended period of time.

33. The method of claim 32 including performing steps (a)–(g) of claim 31 for a plurality of patients during said extended period of time.

34. The method of claim 32, including the further step of automatically determining the average time between each said incident message and the next succeeding reset message, separately with respect to a plurality of patients.

35. The method of claim 32, including the step of automatically limiting the duration of transmission of an incident message.

36. The method of claim 32, including the further steps of automatically recording the time of receipt of each incident message and each reset message and automatically recording the identity of the particular one of a plurality of sensor transmitters from which each incident message and each reset message is received.

37. A method for obtaining and arranging patient data, comprising:
   (a) placing an absorbent pad in position to receive and absorb a quantity of electrically conductive fluid from a patient;
   (b) placing electrodes connected to a signaling device adjacent said absorbent pad in position to be interconnected electrically by a quantity of electrically conductive fluid absorbed by said absorbent pad;
   (c) applying an electrical potential between said electrodes and detecting electrical current conducted between said electrodes by said electrically conductive fluid absorbed in said absorbent pad;
   (d) in response to detecting said electrical current between said electrodes, transmitting an encoded incident message;
   (e) receiving said encoded incident message at a location remote from said absorbent pad and recording the time of receipt of said incident message;
   (f) thereafter removing said absorbent pad and replacing it with one that is free from electrically conductive fluid absorbed therein, placing said absorbent pad in position to receive and absorb a further quantity of electrically conductive fluid from said patient, and contemporaneously transmitting an encoded reset message;
   (g) calculating the amount of time between each incident message and the next succeeding reset message;
   (h) automatically recording the time of receipt of each incident message and each reset message and automatically recording the identity of the particular one of a plurality of sensor transmitters from which each incident message and each reset message is received;
   (i) identifying and recording in a computer database a digitally-encoded photograph of a patient together with data relating the times of receipt of incident messages and reset messages relating to that patient in a manner permitting identification and retrieval of said photograph together with said data relating to times of receipt of incident messages and reset messages relating to that patient; and
   (j) repeating steps (b), (c), (d), (e), and (f) throughout an extended period of time.

38. The method of claim 36, including the step of recording patient medical history data in said database in a manner permitting identification and retrieval thereof together with said data relating to times of receipt of incident messages and reset messages.

39. A system for detecting the presence of electrically conductive fluid in any of a plurality of locations, comprising:
   (a) a plurality of detectors, each including:
      (i) a first layer of a flexible fluid-absorbent sheet material;
      (ii) a pair of elongate flexible electrodes extending generally parallel with each other and spaced apart from each other, each of said electrodes being attached to said first layer and each of said electrodes having a medial longitudinal margin and a lateral longitudinal margin;
      (iii) a second layer of flexible fluid-absorbent sheet material overlying said pair of electrodes and adhered to said first layer along a continuous central strip extending parallel with said electrodes and located between said electrodes, and also adhered to said first layer along a respective strip extending parallel with said electrodes and located alongside said lateral longitudinal margin of each of said electrodes, said first and second layers thereby being interconnected in the form of a pair of separately defined parallel tubes each including one of said electrodes, and each of said electrodes having a respective electrically conductive surface posed within the respective one of said tubes and each said electrode being prevented by said separate parallel tubes from touching said electrically conductive surface of the other flexible electrode of said pair; and (iv) signaling means connected electrically to said electrodes for producing an electrical output signal in response to electrical resistance between said electrodes falling below a predetermined value;

(b) means associated with each signaling means for identifying each signaling means uniquely in said electrical output signal; and (c) means for receiving each said electrical output signal and providing a humanly-perceptible output signal indicative of the origin and time of commencement of each electrical output signal received thereby.

\* \* \* \* \*